(12) United States Patent
Enderle et al.

(10) Patent No.: US 6,415,995 B1
(45) Date of Patent: Jul. 9, 2002

(54) MICRODISPENSING SYSTEM FOR THE OPEN-JET DISPENSING OF LIQUIDS

(75) Inventors: Thilo Enderle, Rheinfelden (DE); Christof Fattinger, Blauen (CH); Gerhard Flury, Binzen (DE); Hans-Peter Hirt, Allschwil (CH); Rene Rietmann, Kaiseraugst (CH); Hansjörg Tschirky, Ettingen (CH)

(73) Assignee: Cybio AG, Jena (DE)

( * ) Notice: Subject to any disclaimer, the term of this patent is extended or adjusted under 35 U.S.C. 154(b) by 0 days.

(21) Appl. No.: 09/708,147

(22) Filed: Nov. 8, 2000

(30) Foreign Application Priority Data

Nov. 9, 1999 (CH) ................................ 2046/99

(51) Int. Cl.[7] .............................. B05B 1/30; B05B 9/00
(52) U.S. Cl. ........................ 239/569; 239/583; 239/584; 239/585.1; 239/585.4; 239/99; 239/124; 251/129.17; 251/129.21
(58) Field of Search ................................. 239/569, 583, 239/584, 585.1, 585.4, 99, 124, 106, 110, 102.2; 222/504, 509, 518, 318, 424, 496; 251/129.17, 129.21, 331

(56) References Cited

U.S. PATENT DOCUMENTS

| | | | | | |
|---|---|---|---|---|---|
| 5,791,631 A | * | 8/1998 | Martin et al. | ........... | 251/331 X |
| 5,820,105 A | * | 10/1998 | Yamaji et al. | ........... | 251/331 X |
| 6,006,728 A | * | 12/1999 | Matsuda et al. | ..... | 251/129.17 X |
| 6,168,136 B1 | * | 1/2001 | Jaasma et al. | ......... | 251/129.17 |

\* cited by examiner

Primary Examiner—Robin O. Evans
(74) Attorney, Agent, or Firm—Reed Smith LLP

(57) ABSTRACT

A microdispensing system is useful for the open-jet dispensing of liquids. A valve having a valve chamber is bounded by an impermeable elastic membrane and is filled with the liquid for dispensing. One or more liquid supply lines lead to the valve chamber. An outlet closed from the exterior by the membrane in the position of rest leads from the chamber to a dispensing nozzle. An actuator chamber is disposed on the other side of the membrane. In the actuator chamber, an electromechanical drive is connected to the membrane for the purpose of briefly lifting the membrane from the outlet. The actuator chamber is closed in such manner that it can be subjected to a pressure differing from atmospheric pressure.

6 Claims, 6 Drawing Sheets

MICRODISPENSING SYSTEM FOR THE OPEN-JET DISPENSING OF LIQUIDS

BACKGROUND OF THE INVENTION

1. Field

The invention relates to the field of microdispensing systems for open-jet dispensing of liquids.

2. Description

Open-jet dispensing systems consist of a dispensing nozzle, a liquid supply line to the dispensing nozzle, and a dispensing drive.

Different operating principles are known for the dispensing drive in microdispensing systems and piezo-actors, bubble-jet actors, electrostatic, pneumatic and magnetostrictive drives are in practical use. Important uses of these drives are in inkjet printing and micropipetting.

For dispensing biological liquids and suspended cells it is important that no or minimal shearing forces, pressure and temperature influences occur. The waste heat of known electromechanical drives can have an adverse effect on the stability of protein and enzyme solutions during dispensing. Consequently, known drives can be used only to a limited degree.

Moreover, before dispensing most known microdispensing systems have to be vented and initialized by dispensing runs. After dispensing, each microdispensing system must be emptied, flushed and cleaned. Because it is extraordinarily important to use sparingly the usually expensive liquids and because known microdispensing systems can be initialized, emptied or flushed only by a large number of dispensing runs with repeated drive actuation followed by completely discarding the excess liquid, recovery of liquid is nearly impossible.

Cleaning can be a considerable problem in microdispensing systems, especially the dispensing nozzle. Depending on the type of construction, the nozzle cannot be interchanged, making cleaning difficult in the event of contamination or any clogging.

In addition, most known dispensing systems are not made completely from inert materials. In known electromechanical dispensing systems, the drive is often subjected to liquid for dispensing flowing around it. Apart from the mentioned heating problem, this can lead to contamination of the liquid and incorrect drive operation due to soiling.

Another disadvantage of known open-jet dispensing systems is that the quantity dispensed per run is predetermined by the construction and is influenced by the viscosity and surface tension of the liquid for dispensing. In view of the above problems, there has been a long felt need for an invention that addresses these concerns.

SUMMARY OF THE INVENTION

The subject invention provides a microdispensing system for open-jet dispensing a liquid. This system comprises a valve, at least one liquid supply line, an outlet, a dispensing nozzle, an actuator chamber, and an electromechanical drive. The valve has a chamber that is formed at least in part from a liquid-impermeable elastic membrane that can be stretched from a resting position to a stretched position. The valve chamber is filled with the liquid to be dispensed. At least one liquid supply line is in liquid communication with the valve chamber. This at least one supply line is configured and dimensioned for supplying liquid to the valve chamber. The outlet is open to liquid communication with the valve chamber when the elastic membrane is in the stretched position C losed to liquid communication with the valve chamber when the elastic membrane is in the resting position. The outlet is configured and dimensioned so that when the elastic membrane is in the stretched position, liquid from the valve chamber enters the outlet. The dispensing nozzle is configured and dimensioned to be in liquid communication with the outlet and to open-jet dispense liquid. The dispensing nozzle is constructed so that when liquid flows from the outlet into the dispensing nozzle, it is open-jet dispensed from the dispensing nozzle. The actuator chamber located adjacent the elastic membrane on the side of the membrane opposite the valve chamber. The actuator chamber is configured and dimensioned to be pressure-tight and to retain a pressure differing from atmospheric pressure. The electromechanical drive is located within the actuator chamber and is connected to the membrane. The electromechanical drive is constructed so that when actuated, it stretches the membrane from the resting position to the stretched position, thereby allowing liquid from the valve chamber to enter the outlet and to be open-jet dispensed through the dispensing nozzle.

BRIEF DESCRIPTION OF THE FIGURES

Details and preferred features of the invention will be apparent from the accompanying drawings, which illustrate preferred exemplified embodiments and in which.

DETAILED DESCRIPTION OF THE PREFERRED EMBODIMENTS

The invention will now be described in terms of its preferred embodiments. These embodiments are set forth to aid in understanding the invention but are not limiting.

The invention relates to a microdispensing system for the openjet dispensing of liquids, with a valve having a valve chamber bounded by an impermeable elastic membrane and filled with the liquid for dispensing, a liquid supply line leading to said valve chamber while an outlet closed from the exterior by the membrane in the position of rest leads from said chamber to a dispensing nozzle.

For the purpose of this description, the term "microdispensing" is used to denote the dispensing of volumes of liquid in the region of 10 microliters and less. The term "openjet dispensing" denotes dispensing in which the dispensing nozzle and the target are separated by an air gap in order to avoid contamination.

The invention provides a rugged and inert dispensing system by which microvolumes of liquids having diverse physico-chemical properties can be delivered to the target without contamination, with minimum loss, and with a preselected dispensed volume without any substantial influence from shearing forces, increased temperatures and pressure waves.

To this end, an actuator chamber is disposed on the other side of the valve membrane and in said actuator chamber there is provided an electromechanical drive connected to the membrane for the purpose of briefly lifting the membrane from the outlet, and said actuator chamber is closed in pressure-tight relationship in such manner that it can be subjected to a pressure differing from atmospheric pressure. The valve has two supplies that allow venting lushing and recovery of the liquid for dispensing without actuating the dispensing drive. The dispensing nozzle is made from an inert and hydrophobic elastomer, and this prevents clogging and facilitates cleaning.

Figure 1:
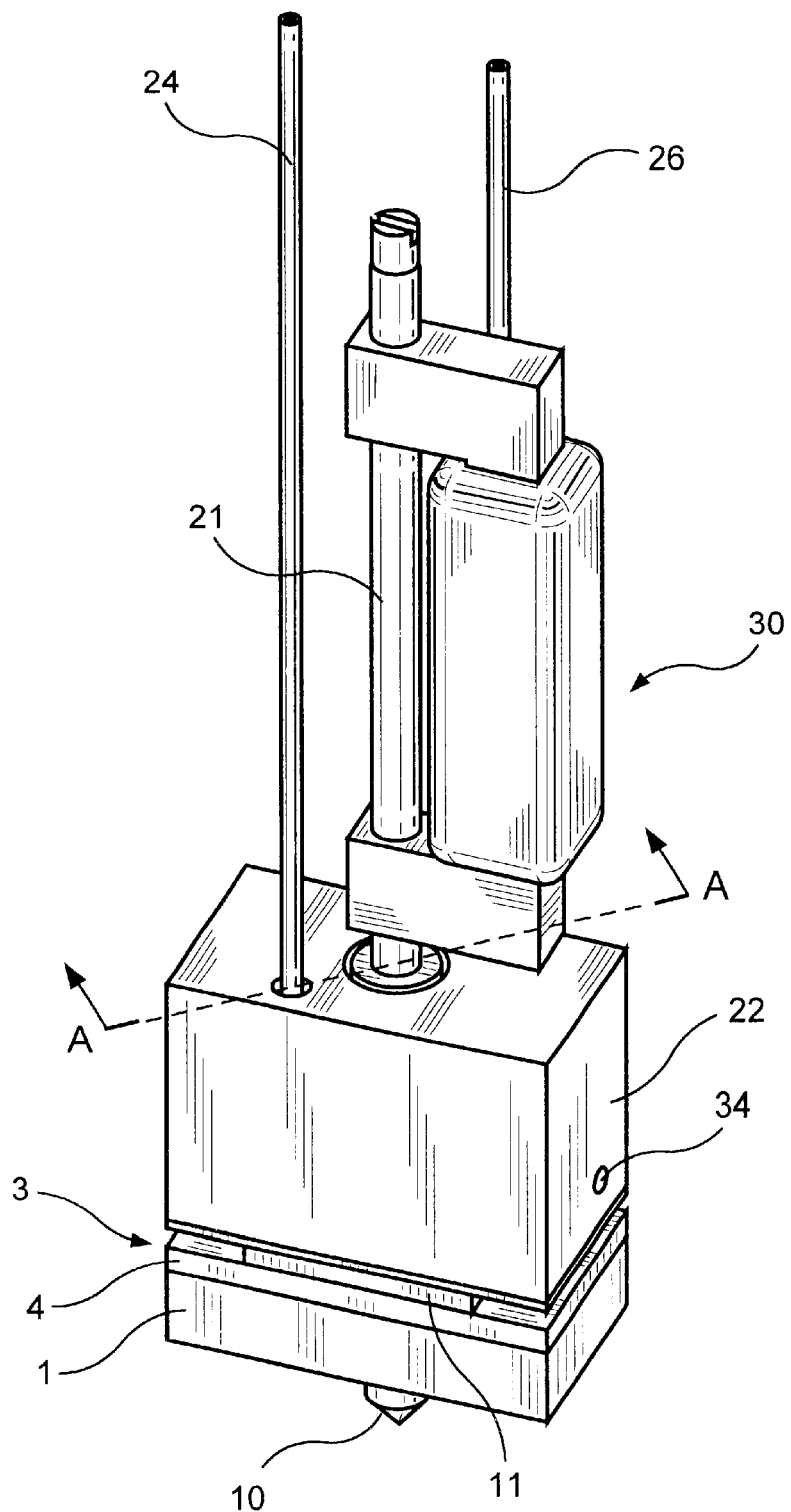
FIG. 1 a perspective view of a single microdispensing device.
Figure 2:
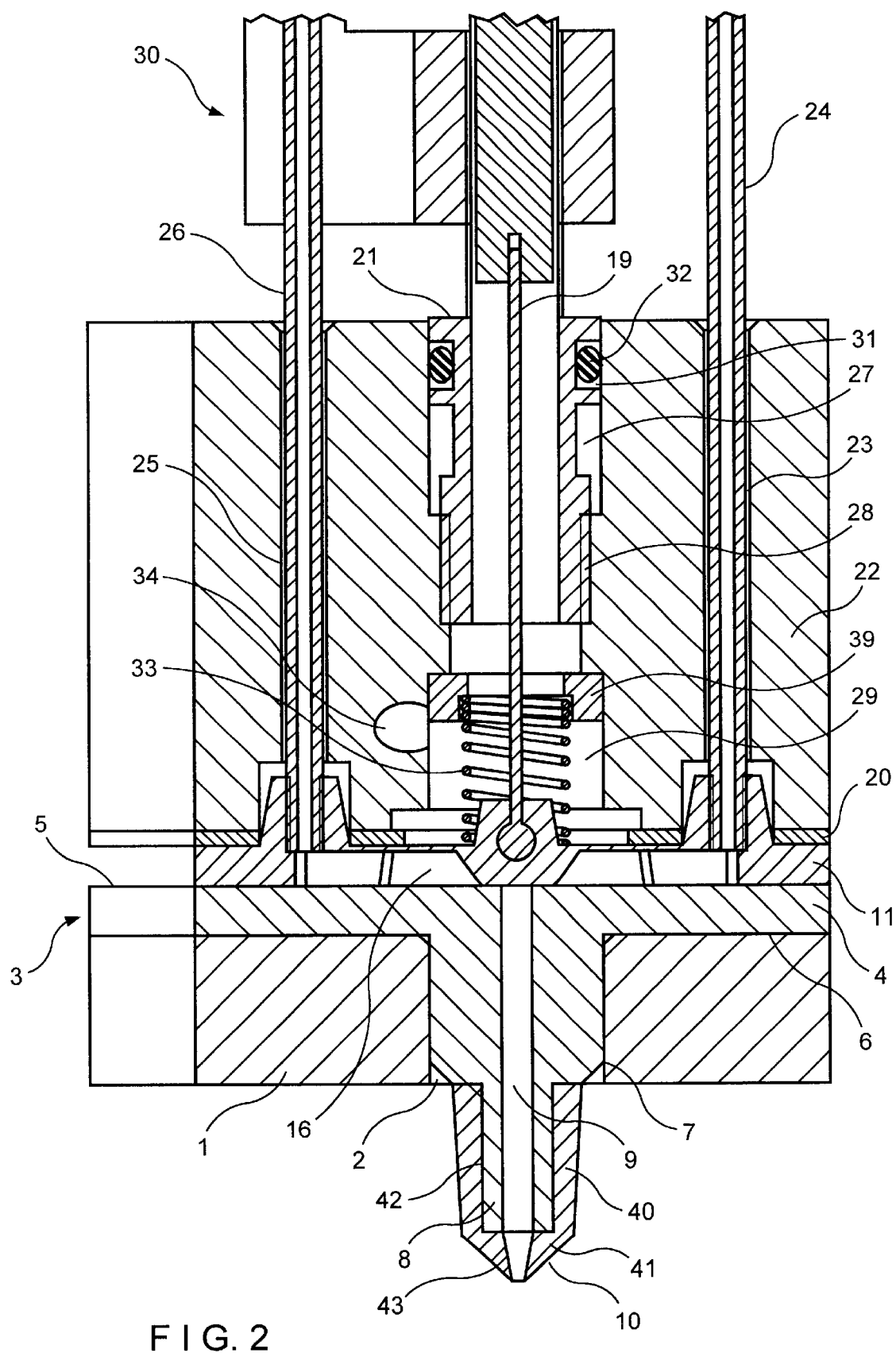
FIG. 2 a section on the plane defined by the line A—A in FIG. 1.

As will be seen from FIGS. 1 and 2, a rectangular base plate I has a central bore 2. A dispensing nozzle element 3 has a rectangular top part 4 with a flat top surface 5 and a likewise flat bottom surface 6, and a cylindrical bottom part 7 with an extension 8 constructed in the form of a capillary tube. A bore 9 extending from the top surface 5 through the entire element leads into the bottom end of the extension 8. The extension 8 is provided with an interchangeable elastic dispensing nozzle 10 with a capillary passage.

The dispensing nozzle element 3 rests with its bottom surface 6 on the base plate, and the bottom part 7 with the extension 8 extends through the bore 2.

Figure 6A:
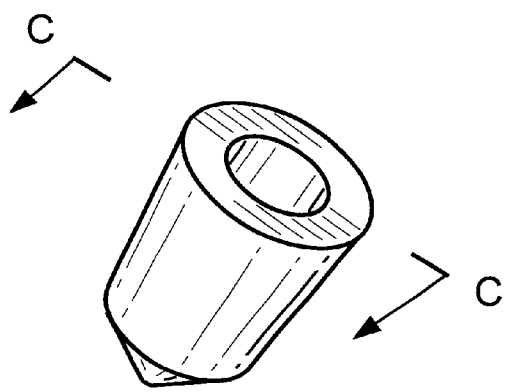
FIG. 6 a perspective view of the dispensing nozzle from above (6a), from below (6b) and in section (6c) on the line C—C.
Figure 6B:
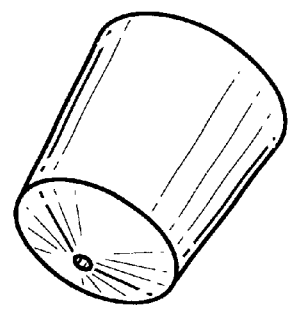
Figure 6C:
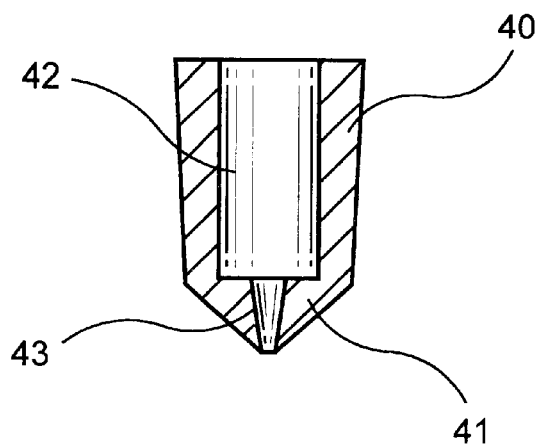

As shown in FIG. 6, the dispensing nozzle 10 consists of a cylindrical part 40 and a conical part 41, both of which are provided with a central bore 42,43. The central bore 42 in the cylindrical part has a diameter such that the dispensing nozzle can be pushed on to the capillary tube 8. In the conical part, the central bore 43 tapers from a diameter corresponding to the bore 9.

The dispensing nozzle is made from an inert hydrophobic elastomer. The elastic properties prevent the nozzle from clogging and facilitate cleaning without having an adverse effect on the open-jet dispensing of the small volumes of liquid. Also, the elastic dispensing nozzle is much less sensitive to mechanical damage than prior art dispensing nozzles made of glass or other hard materials.

Advantageously, for production and handling reasons, a plurality of or all the dispensing nozzles for a dispensing line or a dispensing array are connected to form a unit.

Figure 5A:
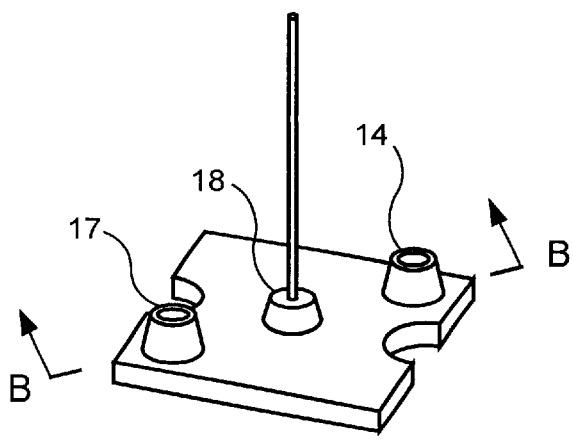
FIG. 5 a perspective view of a membrane element from above (5a), from below (5b) and in section (5c) on the line B—B.
Figure 5B:
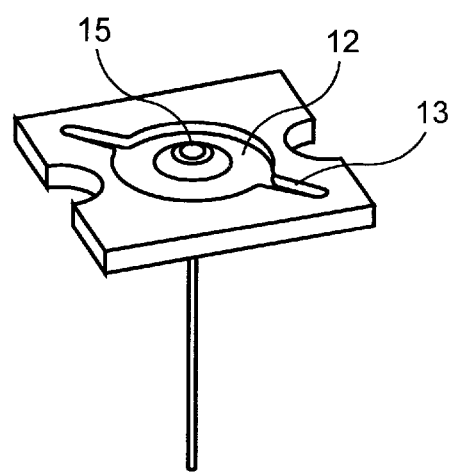
Figure 5C:
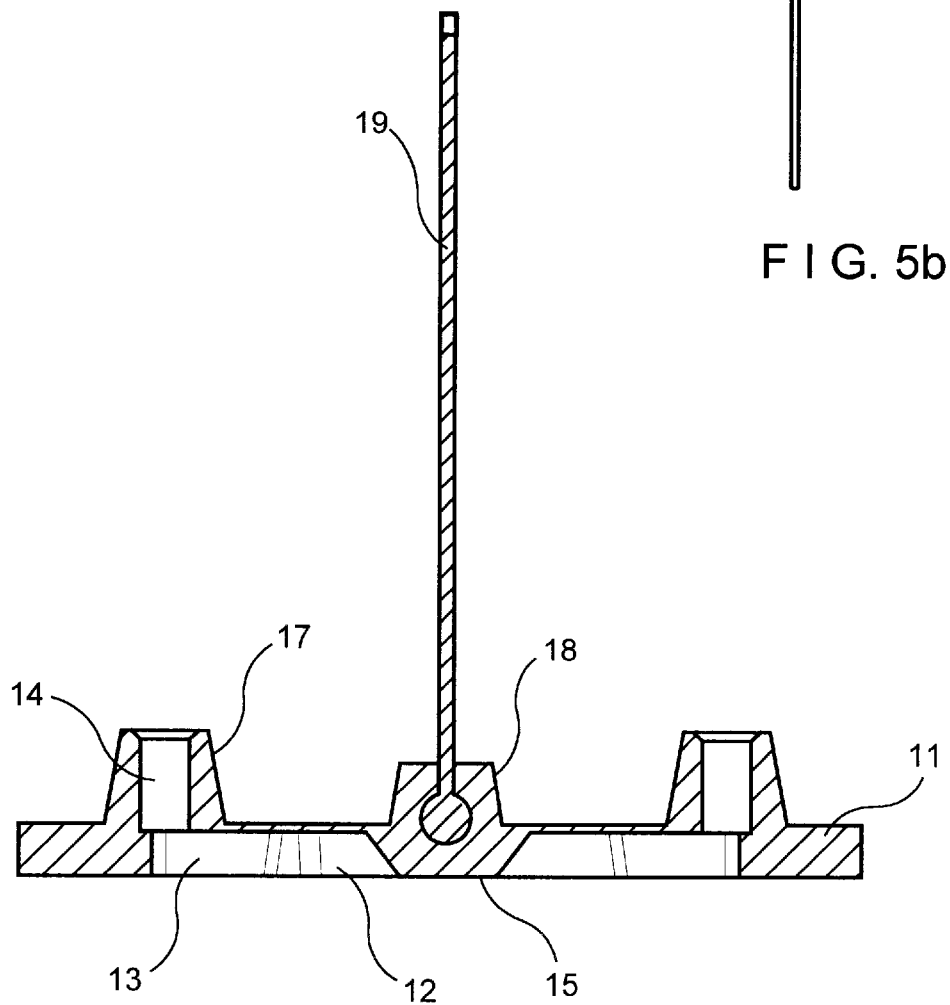

As shown in detail in FIG. 5, a membrane element 11 is substantially disc-shaped and has substantially identical dimensions to the dispensing nozzle element 3. In its bottom surface, the membrane element has a concentric annular recess 12 and two ducts 13 disposed opposite one another and connecting the annular recess to off-center bores 14, which further outwards pass through the membrane element 11 in parallel relationship to the axis. The center surrounded by the recess 12 is formed by a truncated cone 15. The membrane element 11 rests by its bottom surface on the top surface of the dispensing nozzle element. In this position, the annular recess 12 and the ducts 13 form a chamber 16 around the truncated cone 15, the flat bottom surface of which covers the bore 9. The chamber 16 is designated as valve chamber.

The top surface of the membrane element has collar-shaped sealing lips 17 surrounding the bores 14 and a central thickening 18 which is directed axially upwards and into which there is cast an elongate cylindrical axially disposed extension 19 of metal. A sealing disc 20 made from an elastomer adjoins the membrane element 11 on the side of the top surface thereof. The sealing disc has a rectangular shape of substantially the same size as the base plate 1 and is provided with bores to receive the sealing lips 17 and a central bore corresponding approximately to the outside diameter of the annular recess in the underside of the membrane element.

A block 22 adjoining the sealing disc 20 serves to accommodate the supply lines and the actuating device for the valve. The block has two bores 23,25 which are concentric with the off-center bores 14 of the membrane element 11 and the corresponding bores of the sealing disc 20 and through which extend two supply capillaries 24,26 both of which lead by their bottom ends into the off-center bores 14 surrounded by the sealing lips 17 and are thus in communication with the chamber 16.

In their bottom part, the off-center bores 23,25 in the block 22 have a widened diameter to receive the sealing lips 17. The remaining part of the bores is adapted to the capillaries 24,26.

A central bore 27 in the block 22 has a narrower middle zone provided with a screw thread 28 and zones which widen out upwardly and downwardly. In the downward direction a two-stage widening is provided, the bottom diameter of which again corresponds to the outside diameter of the annular recess in the membrane element. These widened diameters form a chamber 29 above the membrane element 11 around the thickening 18, said chamber 29 being situated on the drive side of the membrane element and hence being designated in actuator chamber. The actuator chamber is separated from the valve chamber 16 by the thin zone of the membrane element in the region of the recess 12, which zone thus forms a membrane.

The substantially tubular housing 21 of a drive element 30 for the valve is inserted in the central bore 27. A known solenoid drive is used as the drive element. The housing 21 has in its middle zone a thickening with a suitable external screw thread for screwing it into the screw thread 28 of the bore. A peripheral groove 31 to receive an O-ring 32 is also provided in the thickened zone and seals off the bore 27 and hence the chamber 29 from the exterior.

A cylindrical disc 39 is pressed into the bottom part of the central bore 27. A spiral spring 33 extends from the underside of the disc 39 as far as the top surface of the membrane element. In the installed condition the spring 33 is stressed so that it presses the truncated cone 15 of the membrane 11 on to the top surface 5 of the dispensing nozzle element 3.

From the outside of the block 22 a bore 34 leads to the chamber 29.

During operation, a liquid substance for dispensing flows through the capillary 26 into the chamber 16 and out of the chamber via the capillary 24. The chamber 16 is thus permanently filled with the liquid substance. To dispense a specific volume through the dispensing nozzle 10, the membrane is briefly pulled upwards by means of its extension 19 through the agency of an electrical pulse to the solenoid drive, and the bore 9 in the dispensing nozzle element 3 is thus released. Substance can flow out during this opening of the bore 9. When the solenoid drive again releases the membrane, it drops as a result of the spring and its own elasticity and closes the bore. The volume that flows out depends linearly on the duration of the opening of the bore. By varying the duration of the electrical pulse it is possible to change the valve opening time and set the dispensed quantity to a predetermined value.

The membrane movement takes place extraordinarily quickly, so that the opening and closing processes are very short. This leads to very high precision during dispensing.

Through the bore 34 in the block 22 to the chamber 29 above the membrane 11 it is possible to subject this chamber to a working pressure adapted to the pressure in the chamber 16. This enables the relative pressures between the chamber 29 and chamber 16 and their difference from the external atmospheric pressure to be freely selected. For example, in the case of an excess pressure of 1 bar in the chambers 16,29 the membrane 11 is relieved of load so that extremely short opening and closing times are obtained together with high dispensing precision for small dispensed quantities.

The double supply to the chamber 16 enables the valve to be vented and flushed without actuating the drive. The reagents fed via capillary 26 can also be recovered via the capillary 24 on emptying the valve.

The local separation of the electromechanical parts 19,21, 30,33 from the fluidics consisting of the capillaries 24,26 and the chamber 16 prevents the liquid from being heated by the waste heat of the electromechanical drive 30, any contamination of the liquid, and any corrosion of the electromechanical parts by corrosive liquids.

Figure 3:
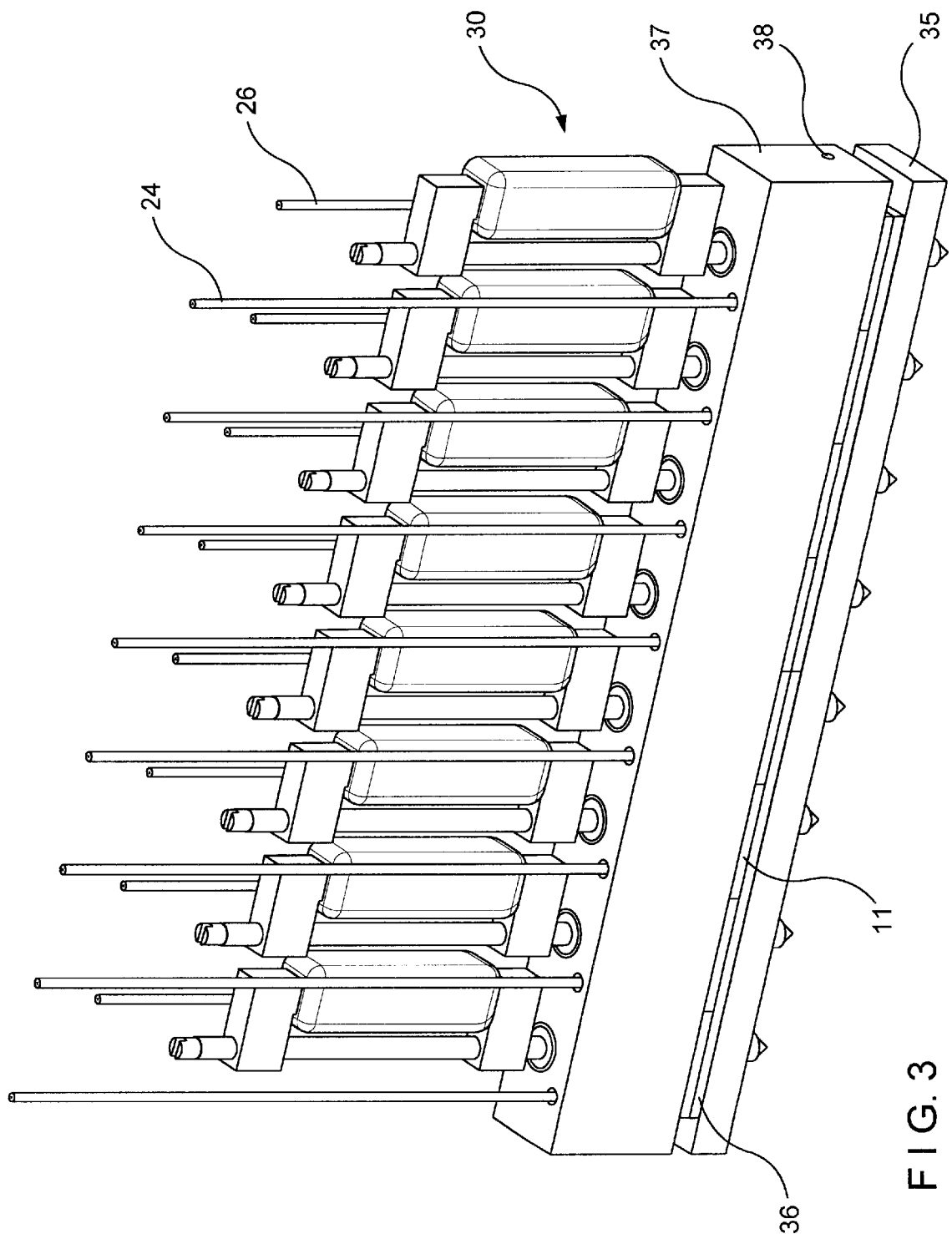
FIG. 3 a perspective view of a unit with eight identical microdispensing devices disposed in line.

As shown in FIG. 3, a plurality of microdispensing valves, eight in the present case, can be disposed in series. For this purpose the base plate 35, the dispensing nozzle element 36 and the block 37 are lengthened accordingly and provided with the corresponding number of bores. The membrane elements can be disposed individually therebetween. Alternatively, a multiple membrane element can be provided. The supply bore 38 for the working pressure is fed to all the chambers through the entire block. The distances between the bores in the base plate and the block correspond to the module used for conventional microliter plates.

Figure 4:
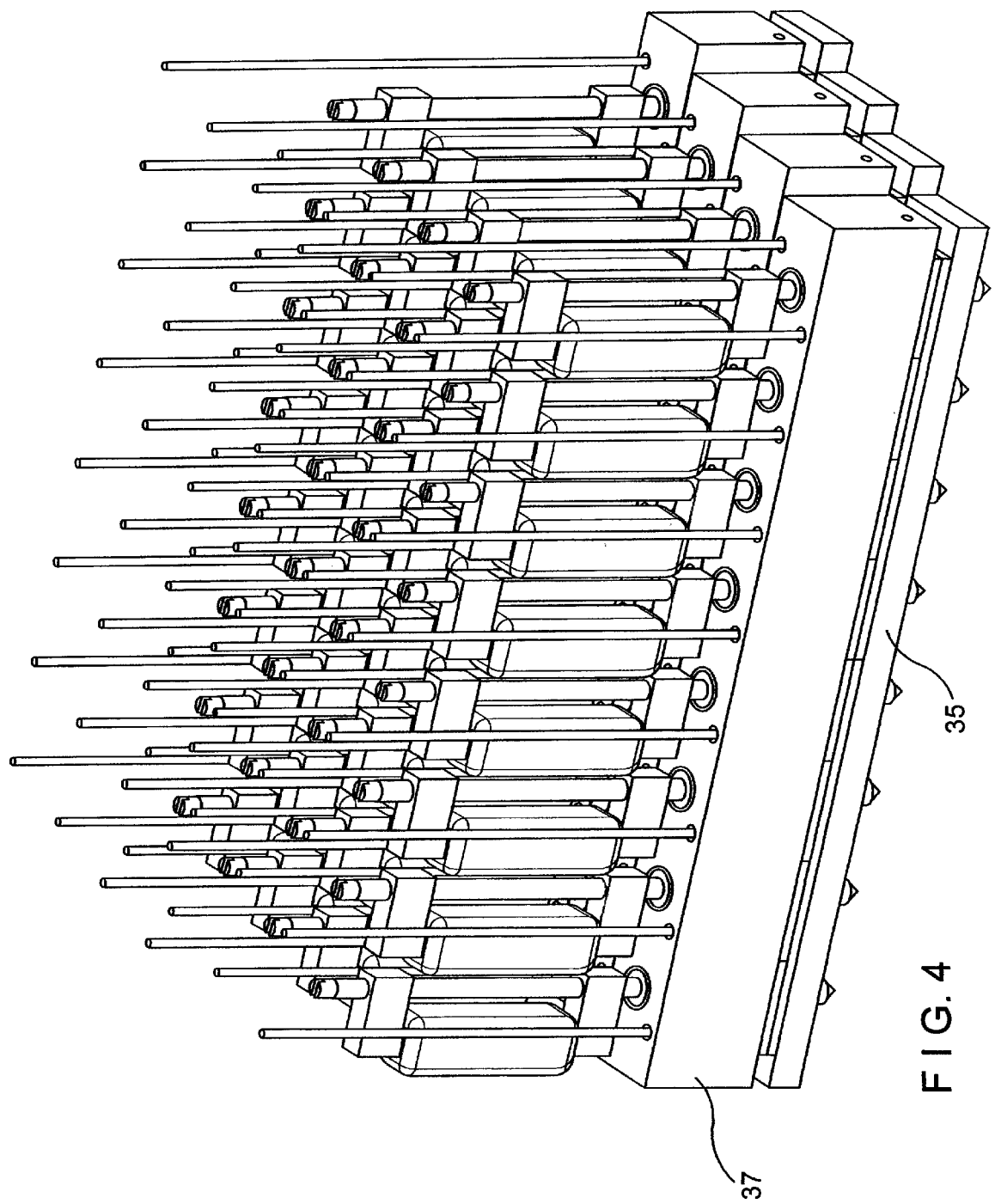
FIG. 4 a system of four units of the kind shown in FIG. 3 disposed side by side.

FIG. 4 shows how a plurality of the elements in series can be combined side by side to form a flat system of 32 dispensing units. The individual series elements are in this case each offset 2.25 millimeter in the longitudinal direction. The module dimension is 9 millimeter. With a system of this kind it is possible to fill high-integration plates with one pass.

The present invention as herein illustrated and described is intended to be representative only, as many changes may be made therein without departing with the clear teachings of the invention. Reference should be made to the following claims in determining the full scope of the invention, as it will be appreciated that the invention is susceptible to modification, variation and change without departing from the proper scope and fair meaning of the appended claims. The invention is to be limited only by the claims that follow and their equivalents.

What is claimed is:

1. A microdispensing system for open-jet dispensing a liquid, which comprises:

(a) a valve having a chamber that is formed at least in part from a liquid-impermeable elastic membrane that can be stretched from a resting position to a stretched position, the valve chamber being filled with the liquid to be dispensed;

(b) at least one liquid supply line in liquid communication with the valve chamber for supplying liquid to the valve chamber;

(c) an outlet that is open to liquid communication with the valve chamber when the elastic membrane is in the stretched position and closed to liquid communication with the valve chamber when the elastic membrane is in the resting position, the outlet allowing liquid flowing out of the valve chamber to pass through the outlet when the elastic membrane is in the stretched position;

(d) a dispensing nozzle which is in liquid communication with the outlet and to open-jet dispense liquid, the dispensing nozzle being constructed so that when liquid flows from the outlet into the dispensing nozzle, it is open-jet dispensed through the dispensing nozzle;

(e) an actuator chamber located adjacent the elastic membrane on the side of the membrane opposite the valve chamber, the actuator chamber being pressure-tight and being contained in a block having a wall with a bore through which a working pressure adapted to the pressure in the valve chamber is applicable to the actuator chamber; and (f) an electromechanical drive located within the actuator chamber and connected to the membrane, the electromechanical drive being constructed so that when actuated it stretches the membrane from the resting position to the stretched position, thereby allowing liquid from the valve chamber to enter the outlet and to be open-jet dispensed through the dispensing nozzle.

2. The microdispensing system according to claim 1, wherein the at least one liquid supply line consists of two supply lines that are configured and dimensioned to allow venting, flushing and recovery of the liquid for dispensing, without the electromechanical drive being actuated.

3. The microdispensing system according to claim 1, wherein the dispensing nozzle is removable and can be interchanged with another dispensing nozzle.

4. The microdispensing system according to claim 1, wherein the dispensing nozzle is made from an inert hydrophobic elastomer.

5. The microdispensing system according to claim 3, wherein the dispensing nozzle is made from an inert hydrophobic elastomer.

6. The microdispensing system according to claim 2, wherein a first conduit connected with the valve chamber allows supply of liquid to the valve chamber, and second conduit connected with the valve chamber allows venting of the valve chamber and removal of liquid from the valve chamber without the electromechanical drive being actuated.

* * * * *

UNITED STATES PATENT AND TRADEMARK OFFICE
Certificate

Patent No. 6,451,995 B1

Patented: September 17, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Nai-Kong V. Cheung, Purchase, NY (US); Steven M. Larson, Washington, DC (US); Hong-Fen Guo, New York, NY (US); and Ken Rivlin, New York, NY (US).

Signed and Sealed this Thirteenth Day of June 2006.

LARRY R. HELMS
*Supervisory Patent Examiner*
Art Unit 1643